United States Patent
Raffer

(10) Patent No.: US 7,275,419 B2
(45) Date of Patent: Oct. 2, 2007

(54) ROTATION RHEOMETER OF VISCOSIMETER

(75) Inventor: Gerhard Raffer, Graz (AT)

(73) Assignee: Anton Paar GmbH, Graz-Strassgang (AT)

( * ) Notice: Subject to any disclaimer, the term of this patent is extended or adjusted under 35 U.S.C. 154(b) by 149 days.

(21) Appl. No.: 11/135,048

(22) Filed: May 23, 2005

(65) Prior Publication Data

US 2006/0000262 A1  Jan. 5, 2006

(30) Foreign Application Priority Data

May 24, 2004  (AT) ............................... A 896/2004

(51) Int. Cl.
*G01N 11/14* (2006.01)
(52) U.S. Cl. .................... 73/54.28; 73/54.01
(58) Field of Classification Search ............... 73/54.28, 73/54.01
See application file for complete search history.

(56) References Cited

U.S. PATENT DOCUMENTS

| | | | |
|---|---|---|---|
| 3,115,769 A | 12/1963 | Bowen, Jr. | |
| 4,173,142 A | 11/1979 | Heinz | |
| 6,167,752 B1 | 1/2001 | Raffer | |
| 6,218,751 B1 * | 4/2001 | Bohlin | 310/90.5 |
| 6,240,770 B1 * | 6/2001 | Raffer | 73/54.28 |
| 6,571,610 B1 * | 6/2003 | Raffer | 73/54.35 |
| 6,698,275 B2 * | 3/2004 | Hall | 73/54.28 |
| 6,952,950 B2 * | 10/2005 | Doe et al. | 73/54.01 |
| 6,959,588 B2 * | 11/2005 | Zougari et al. | 73/61.62 |
| 2004/0173009 A1 | 9/2004 | Doe et al. | |

FOREIGN PATENT DOCUMENTS

| AT | 404 192 B | 9/1998 |
|---|---|---|
| DE | 27 33 099 B1 | 4/1979 |
| DE | 199 11 441 A1 | 9/2000 |
| DE | 102 09 350 A1 | 9/2003 |

\* cited by examiner

*Primary Examiner*—Hezron Williams
*Assistant Examiner*—Rodney Frank
(74) *Attorney, Agent, or Firm*—Laurence A. Greenberg; Werner H. Stemer; Ralph E. Locher

(57) ABSTRACT

A rotational rheometer or viscometer has a measuring motor for driving a measuring shaft which carries a measuring system, particularly a measuring head supported by a shaft portion, which may be contacted with a substance to be examined. Measuring data are introduced into the calculation of the properties, particularly the viscosity, of the substance. The measuring system has a characteristic identification with data referring to its properties, such as the geometry, the type, and/or the construction of the measuring head. An encoder module enables contactless reading the information. The data transmission path between the measuring system and the uptake or receiver unit has at least one section where the data may be transmitted wirelessly or over an air transmission path or air main path.

20 Claims, 2 Drawing Sheets

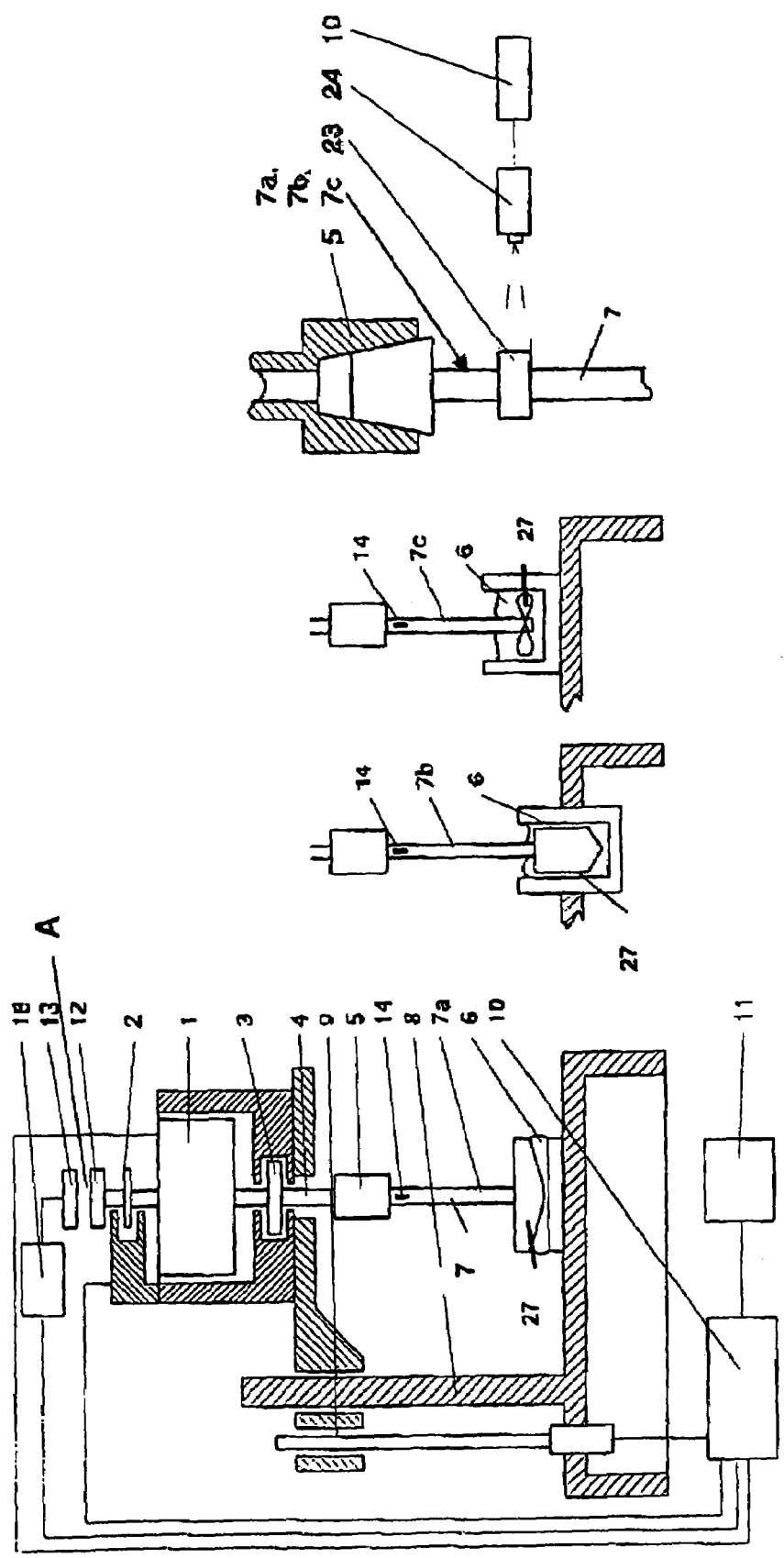

ROTATION RHEOMETER OF VISCOSIMETER

BACKGROUND OF THE INVENTION

Field of the Invention

The invention concerns a rotational rheometer or viscometer comprising a measuring motor for driving a measuring shaft which carries a measuring system, particularly a measuring head supported by a shaft portion, which may be contacted with a substance to be examined, particularly a liquid. The measuring data, particularly electrical parameters of the measuring motor and/or rotational and/or axial movements of the measuring shaft, sensed in the course of a measurement are brought into the calculation of the properties, particularly the viscosity, of the substance.

Rheometers or viscometers of this type are known, for example, from Austrian patent AT-404192 B1 (cf. U.S. Pat. No. 6,167,752), German patent DE 2733099 B1 (cf. U.S. Pat. No. 4,173,142), as well as German DE 19911441 (cf. U.S. Pat. No. 6,240,770).

When designing such rotational rheometers or viscometers, there is the object, above all, to be able to determine the properties of the substances examined with sufficiently high precision as required by rheologists. In this connection, both the influences of temperature, for determining the normal force, and the support of the measuring shaft to be as frictionless as possible play a role. Furthermore, such rotational rheometers or viscometers should be able to be simple in manufacture and should be constructed in a operationally reliable way. In an advantageous manner, such rotational rheometers or viscometers show an air borne measuring shaft in order to be able to absorb rotational and axial movements of the measuring shaft in a frictionless way.

For the measuring motor that drives the measuring shaft, the relation between the torque at the measuring shaft and the current consumption of the measuring motor is known or is determined as precisely as possible by appropriate calibrating measurements. In this way, the moment exerted by the substance to be examined to the measuring shaft via the measuring system can be determined by measuring the current consumption of the measuring motor. Measuring the torque precisely is of paramount importance. Furthermore, the force can be determined that acts in axial direction onto the measuring shaft which, in particular, is effected by measuring the air gap in axial direction in the air bearing of the measuring shaft. Any movement or displacement of the measuring shaft or changes of the thickness of the air gaps are proportional to the axial force exerted to the measuring shaft or are in a mathematical correlation to it. Due to the proportionality or the mathematical correlation, one can conclude to the force exerted by the substance by measuring the torque, and optionally the thickness and/or the change of the air gap, i.e. the change of position and stroke of the measuring shaft in axial direction.

In order to determine the parameters of a sample, it is possible to drive the measuring shaft with a constant number of revolutions and to measure the torque (CSR test). However, it is also possible to drive the measuring shaft with constant torque and to measure the number of revolutions or the rotational position (CSS test). Finally, the measuring shaft may be driven with a rotational movement that is sinusoidal or has another wave form (oscillation test). In this latter experimental procedure, apart form being able to determine the viscous share, one can also determine the elastic component of the sample.

For evaluating the sensed measuring values or the electrical parameters of the measuring motor and/or of the measuring shaft, the geometry of the measuring system plays also an important role. In principle, the different measuring systems are standardized and encompass substantially cone/plate measuring systems, plate/plate measuring systems and cylinder measuring systems. For evaluating the measuring data, it is also important to know the precise values of the geometry of the measuring system used. However, such measuring systems show small, but very influential differences of geometry, particularly due to manufacturing tolerances, which falsify the rheologic results or the measuring results. Above all, it is the torque which is influenced by geometry. Consequently, the geometric values are determined and written down or recorded by the producers of such measuring systems. Then, these recorded values are included into the calculation when evaluating the measuring data or when preparing the measuring results, and thus the different geometries of the measuring systems due to manufacturing tolerances are eliminated.

In FIG. 1, the construction of a rotational rheometer or viscometer of different measuring systems are represented on which the invention is based. In substance, such a rotational rheometer or viscometer comprises a measuring motor 1 which rotates a measuring system 7a, 7b, 7c by means of a shaft 4. The measuring motor 1 has the characteristic that the relation between the torque at the motor shaft and the electric supply, particularly of the current consumption, frequency or phase position, of the measuring motor 1 is known. In this way, the moment of a sample or substance 6 can be determined during a rotational test by measuring the parameter of the electric supply. Moreover, an angular coder 2 is provided to be able to determine the rotational position and the number of revolutions of the shaft 4 for the evaluation. Important is also a bearing for guiding the measuring shaft 4. In accordance with the embodiment and the torque resolution required, antifriction bearings or, as is illustrated in the present case, air bearings 3 are used.

Furthermore, such rotational rheometers or viscometers comprise a stand 8 of a construction that is dimensionally stable as much as possible. The measuring system 7a, 7b, 7c may be displaced to a required level by means of a lifting device 9.

In principle, three different measuring systems of a standardized geometry are used. These different measuring systems comprise cone/plate measuring systems 7a, plate/plate measuring systems and cylinder measuring systems 7b.

In special cases, even non-standardized measuring systems 7c are used, as illustrated in FIG. 1, e.g. realized in the shape of a propeller. These measuring systems of different geometries are either non-positively and/or positively connected to the shaft 4 by a coupling mechanism. In dependence on the application, measuring systems of a different geometry are utilized.

For precisely determining the rheologic characteristic values, apart from measured variables such as number of revolutions, torque, deformation angle and phase position, the knowledge of the precise values of the measuring system geometry is of extraordinary importance. Caused by manufacturing tolerances, even measuring systems of the same construction show small differences of geometry which would falsify the rheologic results. For example in a plate/plate measuring system, the viscosity result is influenced by the fourth order of the plate diameter. In cone/plate measuring systems, the measuring results are influenced, in addition, from the angular variation of cone as well as from the magnitude of the cone diminution. Therefore, all measuring systems are measured on measuring machines by the rheometer producers, and the geometric values are assigned to the measuring systems by a unique serial number or identification which is typical for the respective measuring system. The user has to take care that with every measurement for calculating the rheologic values, the data or measuring system geometry of the measuring system used, that correspond to the serial number or the identification, are input into the calculator system 10, 11.

SUMMARY OF THE INVENTION

It is an object of the invention to provide a rotational rheometer or viscometer of the type described at the outset where the recognition of the measuring system used can automatically be effected, and where the specific geometry data can be transmitted to the calculator system in a manner as simple and as precise as possible and without the help of the user. Transmission of the measuring data and/or of the serial number or the identification should neither influence the rheologic measuring values nor the measuring procedure.

In accordance with the invention, these objects are achieved with a rotational rheometer or viscometer of the type described at the outset by the features given in the characterizing clause of claim 1.

With the design according to the invention, it is possible to read out the data characterizing the measuring system used and to put it at the disposal of the evaluation unit without any intervention into the construction of the measuring arrangement and without any influence to the measuring data accrued so that the data can be taken into consideration when calculating the measuring results. This data transmission, effected in a frictionless and contactless manner, can be utilized for any measuring system used, provided it has such identification which can, in particular, be read out or off by an encoding module of the evaluation unit. Reading the data, that are contained in the identification, can be done at any time during the measuring procedure or can be repeated, unless these data are not temporarily stored in the evaluation unit for the measuring procedure. When manufacturing the measuring systems, one has only to take care that the data of the identification are present in an appropriately readable form, e.g. in an electronically readable form or in a form that may be detected in an optical way.

Conveniently, the characteristics of claims 5 and 6 are realized. The coupling units and coupler units, as provided, serve, on the one hand, for the transmission of data from the memory element to the evaluation unit, or for the energy supply to the memory element in the case an appropriate energy supply is necessary for reading the data out, e.g. for sending data through the antenna unit.

In principle. it is possible to store the data in the memory element in such a form that they are readable to the evaluation unit or the coupling units at the side of the encoder module by an inductive or capacitive influence. In likewise manner, the energy supply could be effected through the coupler units by inductive or capacitive coupling of an energy source, e.g. alternating voltage source, to it. Optical coupling units may read out optically memorized information, e.g. in the form of a bar code. An optical energy supply is possible, for example, by impinging radiation or light from appropriate optical transmitter units to photo-sensitive elements which are assigned to the memory element.

It is not of principal importance at which place on the measuring shaft and/or the measuring part the coupling units or the coupler units are arranged; here only the advantageous construction and arrangement of these units are important. It is advantageous, if the coupling and coupler units of the side of the memory element are located in the upper end region of the measuring shaft, because there is a corresponding free space for arranging the coupling and coupler elements of the side of the evaluation unit. There are definitely advantages, if the coupling and coupler units are arranged in the upper region of the measuring part, because there is also the possibility to arrange corresponding coupling and coupler units of the encoder side. The length of the air transmission path or of the section where a contactless transmission of data or of the energy needed for the memory element will be chosen in accordance with the actual facts. In doing this, it should be considered that the transmission of data should be made in an uninfluenced or identical and faultless way; distances of less than a millimeter or up to several centimeters and more can practically be provided.

Advantageous may also be the characteristics of claim 12, according to which the memory element is connected to the corresponding coupling or coupler units by wire. In an advantageous manner, the wire is lead in the interior of the measuring part and/or of the measuring shaft up to the corresponding element.

In the following, the invention will be described in detail by way of example with reference to the drawings.

BRIEF DESCRIPTION OF THE DRAWINGS

FIG. 1 shows schematically the construction of a rotational rheometer or viscometer that has been designed in accordance with the invention.

FIGS. 3, 4 and 5 represent detail views of embodiments of rotational rheometers or viscometers according to the invention.

DESCRIPTION OF THE PREFERRED EMBODIMENTS

Figure 3:
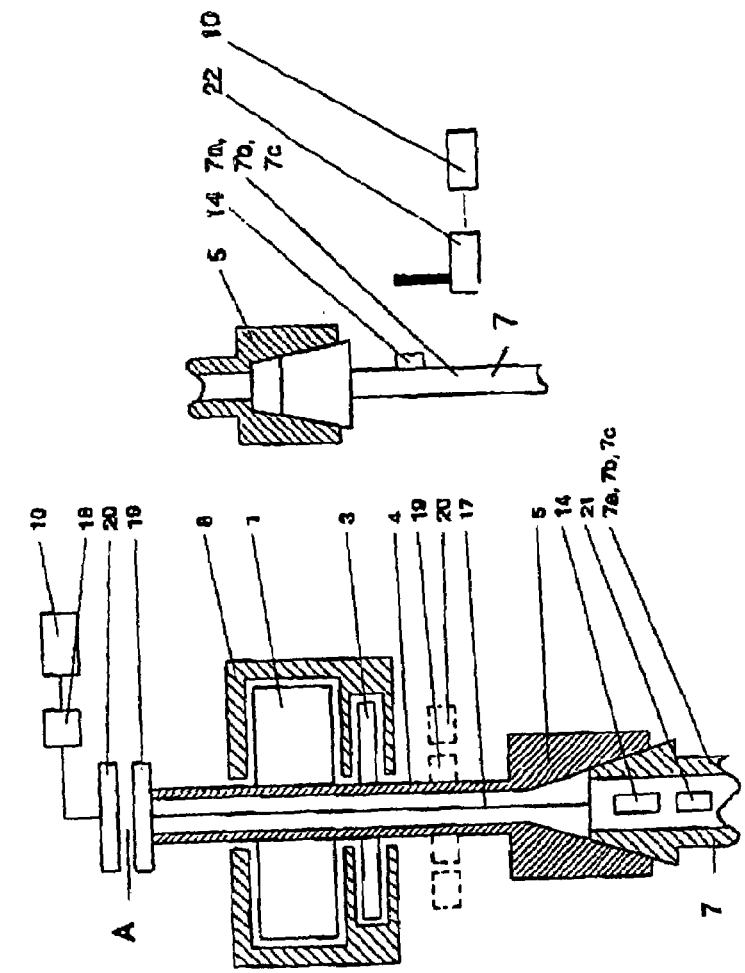

The rotational rheometer or viscometer, in principle formed in a known manner, according to FIG. 1 comprises a processor module 10. The processor module 10 controls or regulates a measuring motor 1 as well as a lifting device 9 and calculates the rheologic basic data and optionally puts an electronic interface to the disposal of an overriding calculator 11 (PC). The measured profile is provided by means of a rheology software, preferably by the overriding calculator 11, and is supplied to the processor module 10 through the interfaces. At that moment, the data of the measuring system 7a, 7b, 7c, as used, including the specific geometry values and other parameters should be known. The respective measuring system 7a, 7b, 7c comprises a carrier or measuring part 7 and a measuring head 27, e.g. in form of a plate, of a cylinder, of a cone, of a propeller or the like.

During a current measuring procedure, the rheologic characteristic values of a substance can be determined and may be transmitted, through the interface, to the overriding calculator 11 which may then carry out some further calculations and, optionally, implements a visualization of the measuring data.

The serial number or identification of the measuring system 7a, 7b, 7c and/or its geometry data are stored in a memory 14, that is optionally a non-volatile one, which is connected to the measuring system 7a, 7b, 7c in an undetachable manner. As a memory element 14, an electronic chip or a mark, such as a bar code or color code, may be used. The transmission of data from the rotating measuring system 7a, 7b, 7c to the evaluation unit 10 is effected through electromagnetic or electric fields (radio system and/or a capacitive and/or inductive coupling) and/or through a transmission medium.

Such a transmission medium is, for example, realized by the coupling elements 12, 13. The coupling element 12 is coupled to the memory element 14 either through a line (not shown here), particularly a bipolar one, and/or through the coupling 5 between measuring shaft 4 and measuring part 7 and the measuring shaft 4. Through an air transmission path A, a coupling element 13 at the side of the evaluation unit is coupled to the coupling element 12 and is, in some cases, also coupled to an encoder module 18, which is optionally connected in series to the evaluation unit 10. Through this air transmission path, that is formed by the coupling elements 12, 13, it is possible to read data from the memory element 14 in a contactless way, to transmit them and to feed them to the evaluation unit 10.

The energy supply of the memory element 14, necessary for reading out the data, can be solved in different ways, e.g. electromagnetically through an antenna and coupling system 19, 20 between the stand 8 and the rotating shaft 4 or the measuring part 7 (FIG. 2), optically by locating a light source on the stand 8 and a photo-sensitive element on the rotating shaft 4, or through a local energy source arranged on the measuring system 7a, 7b, 7c which is realized either as a battery, an accumulator or a condenser.

In principle, reading out the data could also be performed by an inductive coupling including coupling elements 19, 20 which are situated on the measuring shaft 4 in the way as is represented in FIG. 3 above the coupling 5. A corresponding capacitive coupling, which on the one hand serves for reading out the data and, on the other hand, for supplying energy into the memory element 14, may be realized in a comparable manner.

Figure 2:
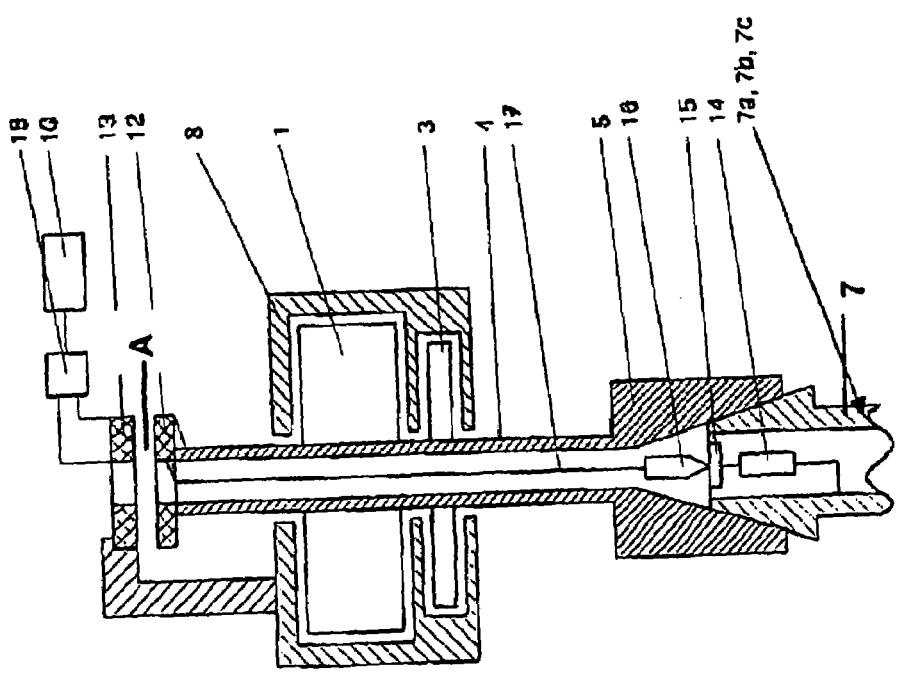
FIG. 2 shows a view of a detail of an alternative embodiment of a rotational rheometer or viscometer according to the invention.

In FIG. 2, an embodiment of a rheometer is illustrated. The memory element 14 is in the interior of the measuring system 7a, 7b, 7c, particularly in the interior of the measuring part 7, and is connected to the measuring part 7 in an electrically conductive fashion. A contact surface 15 of the memory element 14, which is born in an insulated manner, may be connected to a spring-suspended contact 16 supported by the measuring shaft 4 which connects the contact surface 15 through a line 17 to the antenna 12. The return line from the antenna 12 is formed through the rotating shaft 4, through the coupling mechanism 5 and the measuring part 7 to the memory element 14. Both the energy coupling for the memory element 14 and the data transmission to the encoder module 18 mounted on the stand 8 are effected through the antenna 13 mounted on the stand 8. The antennas 12 and 13 represent the coupling and coupler elements for the transmission of data and energy. Such an arrangement or transmitting unit is, in general, known as a transponder system. The processor module 10, by way of the arrangement described, is able both to read data out of the memory element 14, and to write data into the memory element 14 or to supply energy to it, if necessary.

In FIG. 3, an embodiment is shown in which the data transmission and/or the energy supply are effected through the coupling element 19 mounted on the rotating measuring shaft 4, and the coupling element 20 mounted on the stand 8 or the housing. The encoder module 18 communicates with the processor module 10. The coupling system 19 and 20 may be embodied as an electromagnetic antenna system, such as frame antennas, as coupling capacities, or as an optical transmission system, such as in the form of a modulable radiation source and an optical detector. The coupling elements 19 and 20 may be located above the measuring motor 1 or the air bearing 3, as is represented in FIG. 3, or below the same, near the coupling mechanism 5, as is shown in dotted lines.

The transmission medium 17, particularly a wire, connects the memory element 14 with the coupling element 19. The energy supply for the memory element 14 is either effected through the coupling elements 19 and 20, realized as an electromagnetic antenna system, such as frame antennas, coupling capacities and/or as an optical transmission system, e.g. realized as a radiation source on the stand 8 and an optical detector on the rotating shaft 4, or via a local energy source 21, situated on the measuring system 7a, 7b, 7c and realized as a battery, an accumulator or a condenser or a combination of them, wherein energy is transmitted via the coupling system 19, 20 and is supplied in the energy source 21.

Figure 4:
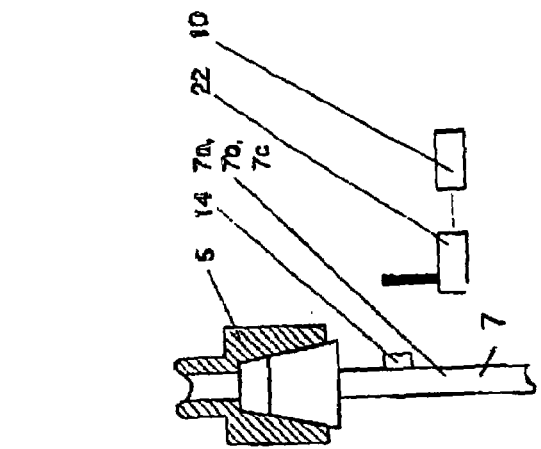

In FIG. 4, an alternative embodiment to FIG. 3 is illustrated. The memory element 14 is situated at the outside of the measuring system 7a, 7b, 7c and communicates with the antenna unit 22 through an electromagnetic field. Energy supply can be effected in the way as shown and described in the context with FIG. 3, or it is supplied by way of the antenna 22, for example.

A further embodiment is shown in FIG. 5. The measuring system 7a, 7b, 7c, particularly the measuring part 7, carries an identification mark 23, realized e.g. as a bar code, a color code or in the form of another optical coding system. By a reading unit 24, realized e.g. as a bar code reader or a camera, the information is transmitted to the processor module 10.

A contactless transmission of data and/or energy between the memory element 14 or the measuring part 7 and/or the measuring head 27 and/or the measuring shaft 4, on the one hand, and the evaluation unit 10 or 11 and/or the encoder 18, on the other hand, may be effected in different ways. In order to guarantee a transmission over an air transmission path, they are advantageously assigned to the respective coupling units for data transmission and/or the coupler units for transmission of energy at the side of the memory element, corresponding coupling units and coupler units being associated to them in a corresponding way at the side of the evaluation unit. It should be taken care that both a contactless transmission of data and, if necessary, a contactless transmission of the energy necessary for transmitting the data can be effected, if an energy storage device is assigned to the memory element 14.

For a contactless transmission of data, transponder systems are known which deliver energy by means of a coupler unit at the side of the evaluation unit, the energy being received by a coupler unit at the side of the memory element. By a coupling unit at the side of the memory element, the information or data are superimposed to the transferred transmitter energy, and can be detected or read out by a coupling element at the side of the evaluation unit. Usually, the energy radiated to the memory element will be influenced by the memory element in such transponder systems, and changes of the energy radiated into the memory element are evaluated with respect to the, thus, transmitted data.

In principle, a transmission of data could also be effected in a similar way as shown in FIG. 2 by optical units. For example, radiation could be sent from the coupling element 13 as the coupler element at the side of the evaluation unit to a corresponding light or radiation sensitive coupling element or coupler element of the memory element 14 via the measuring shaft which is formed as a hollow shaft. In this way, sufficient energy is supplied to the memory element 14 to superimpose an appropriate coding to the reflected radiation by means of a coupling element which can then be correspondingly evaluated by an associated coupling element 13. In a comparable way, the coupling or coupler elements 12 and 13 could transmit energy or data between them, the connection of the coupling or coupler element 12 to the memory element being effected through the wire 17 and/or the measuring shaft 4 and/or the coupling unit 5 and the measuring part 7.

As an optical coupler element, an LED or a laser beam or any other light source could be used which sends a light beam, particularly a beamed one.

In principle, it is also possible to supply energy in an inductive way to a coupling element that is coupled to the memory element 4, and to send the data via an antenna which is powered due to the energy supplied.

In a comparable way, it is also possible to write data into the memory element 4 by means of the coupling elements. Such writing of data into the memory element 4 will be carried out, above all, when initializing this memory element, when the measuring systems 7a, 7b, 7c have been measured. In case that the geometries of the measuring systems should change in some way during their use or some defect occurs in the memory element, the data could be read in anew. For this reason, volatile memories or programmable memories can be used in an advantageous manner as the memory element. This feeding and storing of data is effected with the coupling element provided at the side of the evaluation unit and with the coupling elements at the side of the memory element in a comparable way, as it is provided for reading the data contained in the memory elements.

Reading data into the memory element can be carried out by a central unit or by an evaluation unit. The central unit and the evaluation unit can be combined to form a single unit.

I claim:

1. A rotational rheometer or viscometer, comprising:
   a measuring shaft and a measuring system to be contacted with a substance to be examined, said measuring system being connected to a shaft portion of said measuring shaft;
   a measuring motor for driving said measuring shaft to acquire measurement data for calculating properties of the substance;
   a memory element carried on said shaft portion of said measuring shaft, said memory element storing therein at least one characteristic identification assigned to said measuring system, said characteristic identification containing or comprising, or being configured to receive, data related to properties of said measuring system;
   an evaluation unit for evaluating the measurment data and an uptake or receiver unit disposed for contactless reading in and/or reading out from said evaluation unit;
   cooperating coupling units for bridging an air transmission path between said memory element and said evaluation unit, said coupling units including memory element-side coupling units carried by said measuring shaft; and
   wherein a data transmission path between said measuring system and said uptake or receiver unit includes at least one section wherein the data are transmitted wirelessly or over an air transmission path.

2. The rheometer or viscometer according to claim 1, wherein said memory element is a non-volatile memory to be supplied with data to be stored on said memory element.

3. The rheometer or viscometer according to claim 1, wherein an energy source and said memory element define an energy supply path therebetween for transferring energy required for reading and/or writing data.

4. The rheometer or viscometer according to claim 3, wherein said energy supply path is an air gap.

5. The rheometer or viscometer according to claim 1, which comprises transmission devices for transmitting data over said air transmission path selected from the group consisting of wireless units, inductive units, capacitive units, optical units, and radiation or light sensitive coupling units, said transmission devices communicating with each other, being assigned to said memory element and said evaluation unit or said encoder module.

6. The rheometer or viscometer according to claim 1, which comprises cooperating coupler units respectively assigned to said memory element and to an external energy source for supplying energy to said memory element over said air transmission path.

7. The rheometer or viscometer according to claim 6, wherein said coupler units are selected from the group consisting of wireless units, inductive units, capacitive units, optical units, radiation units, and light sensitive units, disposed to communicate or interact with one another.

8. The rheometer or viscometer according to claim 1, which comprises an energy source selected from the group consisting of at least one accumulator, a battery, and a capacitor assigned to said memory element.

9. The rheometer or viscometer according to claim 8, wherein said energy source(s) is disposed in an interior of said shaft portion.

10. The rheometer or viscometer according to claim 1, wherein said coupling units at an evaluation unit-side are disposed on at least one of a stand bracing said measuring shaft and a housing.

11. The rheometer or viscometer according to claim 1, wherein said characteristic identification or a memory element containing said characteristic identification is disposed on an outer surface of or inside said shaft portion.

12. The rheometer or viscometer according to claim 1, wherein said encoder module is coupled to or integrated in said evaluation unit.

13. The rheometer or viscometer according to claim 1, which comprises a wire connection formed with at least one wire connecting said memory element to a respective said coupling unit carried by said shaft portion and/or said measuring shaft, for exchanging data and/or for supplying energy.

14. The rheometer or viscometer according to claim 13, wherein said coupling units are disposed on an outer surface of one of said shaft portion and said measuring shaft.

15. The rheometer or viscometer according to claim 13, wherein said at least one wire extends through an interior of said shaft portion and/or said measuring shaft and/or along an outer surface of said shaft portion and/or said measuring shaft to a portion of said measuring shaft above or below said measuring motor or a bearing of said measuring shaft, in which said coupling unit(s) are disposed.

16. The rheometer or viscometer according to claim 1, wherein said memory element is supported by said measuring part and at least one wire connects said memory element through at least one contacting unit.

17. The rheometer or viscometer according to claim 16, wherein said memory element is disposed in an interior of said measuring part, said wire extends through said measuring shaft, and said contacting unit is an elastic contact supported by said measuring shaft.

18. The rheometer or viscometer according to claim 1, wherein said memory element is in contact with a memory element-side coupling unit and at least one connection to said measuring shaft and/or said measuring part through at least one wire.

19. The rheometer or viscometer according to claim 18, wherein said at least one wire is a circuit-closing return wire.

20. The rheometer or viscometer according to claim 1, wherein said memory element comprises a volatile memory for changeably storing therein data related to at least one of a geometry, a type, and characteristics of said measuring system.

* * * * *